US012805839B2

(12) United States Patent
Takeda et al.

(10) Patent No.: US 12,805,839 B2
(45) Date of Patent: Nov. 24, 2026

(54) ULTRASONIC PROBE

(71) Applicant: GE Precision Healthcare LLC, Waukesha, WI (US)

(72) Inventors: Kotaro Takeda, Hino (JP); Rajeev Mandwal, Zipf (AT); Atsushi Tsujimoto, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/190,125

(22) Filed: Apr. 25, 2025

(65) Prior Publication Data

US 2025/0331818 A1 Oct. 30, 2025

(30) Foreign Application Priority Data

Apr. 25, 2024 (JP) ................................ 2024-071894

(51) Int. Cl.
*A61B 8/00* (2006.01)
*G10K 11/30* (2006.01)

(52) U.S. Cl.
CPC ............ *A61B 8/4444* (2013.01); *A61B 8/546* (2013.01); *A61B 8/4422* (2013.01); *G10K 11/30* (2013.01)

(58) Field of Classification Search
CPC ............................ A61B 8/4444; A61B 8/4455
See application file for complete search history.

(56) References Cited

U.S. PATENT DOCUMENTS

2021/0121159 A1* 4/2021 Bertocci .............. A61B 8/4483
2022/0395256 A1* 12/2022 Løype .................... A61B 8/546

FOREIGN PATENT DOCUMENTS

JP 2022513501 A 2/2022

OTHER PUBLICATIONS

JP application 2024-071894 filed Apr. 25, 2024—Office Action issued Jul. 2, 2025; Machine Translation; 8 pages.
JP2022513501A English Abstract; Espacnet.com Patent Translate; Oct. 2, 2025; 1 page.

* cited by examiner

*Primary Examiner* — Rochelle D Turchen

(57) ABSTRACT

An ultrasonic probe including an ultrasonic transducer, a metallic inner housing thermally connected to the ultrasonic transducer, and a probe case surrounding the inner housing. The bond lines of the probe case and the bond lines of the inner housing are offset in height from each another.

20 Claims, 10 Drawing Sheets

ULTRASONIC PROBE

CROSS-REFERENCE TO RELATED APPLICATION

This application claim priority to Japanese Patent Application No. 2024-071894, which was file on Apr. 25, 2024 at the Japanese Patent Office. The entire contents of the above-listed application are incorporated by reference herein in their entirety.

TECHNICAL FIELD

The present invention relates to an ultrasonic probe, and more particularly to an ultrasonic probe having a sealed internal space.

BACKGROUND

When performing an ultrasonic examination, an operator can dispose an ultrasonic probe at any position on a scan target, orient the probe in any direction, perform imaging, and obtain a non-destructive/non-invasive ultrasound image.

After such an ultrasonic inspection, various types of grime, contaminants, and the like may adhere to the ultrasonic probe, and bacteria may proliferate. To prevent these problems from occurring and to prolong the lifespan of the ultrasonic probe, ultrasonic probe manufacturers provide users with guides for cleaning, disinfecting, and sterilizing the ultrasonic probe. According to the cleaning, disinfecting, and sterilizing guidelines, the surface of the ultrasonic probe is scrubbed with a sponge, washed with cleaning water, or immersed in a disinfectant solution for several minutes to several hours. Additionally, in certain ultrasonic probe applications, steam may be applied to disinfect and clean the ultrasonic probe. Therefore, the internal structure of the ultrasonic probe is covered by a probe case made of a material that is highly resistant to chemicals and heat, and has the required rigidity. The material of the probe case is a resin such as ABS resin (acrylonitrile, butadiene, styrene copolymer synthetic resin), or the like.

On the other hand, the ultrasonic transducer included in the ultrasonic probe vibrates in response to an applied voltage and generates heat because it is a constituent element that generates ultrasonic waves. In order to dissipate heat generated by the ultrasonic transducer, the ultrasonic probe may be provided with a metal inner housing that is thermally connected to the ultrasonic transducer. Since the inner housing must have high thermal conductivity, it must be manufactured using a metal having high thermal conductivity, such as aluminum or copper.

When manufacturing an ultrasonic probe having a metal inner housing built into this type of resin probe case, an assembly method can be used in which the inner housing and the probe case are made independently, and then joined to complete the inner housing and the probe case. Specifically, a printed circuit board on which electronic components that perform functions such as signal processing of ultrasonic data are arranged is connected to a cable at a back end, and is connected to a transducer module at a front end. Next, an upper surface side portion and the bottom surface side portion of the inner housing are also bonded together so as to enclose or interpose the components of the printed circuit board. Next, the upper surface side portion and the bottom surface side portion of the probe case are also bonded together so as to enclose or interpose the inner housing.

The inner housing, which is divided into an upper surface side portion and a bottom surface side portion, and the probe case can be bonded together using a water-resistant adhesive such as a polyvinyl chloride (PVC) resin-based adhesive, an epoxy resin-based adhesive, and the like. However, the bond line where the upper surface side portion and the bottom surface side portion are joined together may become a path for liquids such as disinfectants, cleaning fluids, and the like to seep in if deterioration occurs due to factors such as aging and the like.

Furthermore, plastics such as polyvinyl chloride, epoxy resins, and the like, and natural rubbers are gas permeable, and even if the adhesive is not degraded, passage of water vapor contained in the air cannot be completely blocked. Water vapor that enters the inside of the ultrasonic probe condenses into liquid water when the internal temperature drops below a dew point. When liquid water comes into contact with electronic components or wiring, short circuits might be induced, and corrosion of metal parts might also occur. A similar problem occurs with chemicals.

SUMMARY

In a first aspect of the present disclosure, an ultrasonic probe is provided. The ultrasonic probe includes an ultrasonic transducer provided at the front end of the ultrasonic probe, a probe case, an inner housing provided inside the probe case, and an electronic circuit connected to the ultrasonic transducer and provided inside the inner housing. The probe case includes an upper surface and a bottom surface facing each other, and a first side surface connected to the upper surface and the bottom surface. The upper surface and the bottom surface of the probe case both have a width greater than the height of the first side surface of the probe case. The probe case has at least an upper surface side portion and a bottom surface side portion. The upper surface side portion of the probe case includes the upper surface of the probe case, and the bottom surface side portion of the probe case includes a bottom surface of the probe case. The upper surface side portion and the bottom surface side portion of the probe case are joined together at a first bond line to form the first side surface of the probe case. The first bond line of the probe case is provided on the first side surface and extends between the front end of the ultrasonic probe and the back end of the ultrasonic probe. The inner housing includes an upper surface and a bottom surface that face each other, and a first side surface connected to the upper surface and the bottom surface. The upper surface and the bottom surface of the inner housing both have a width greater than the height of the first side surface of the inner housing. The inner housing has at least an upper surface side portion and a bottom surface side portion. The upper surface side portion of the inner housing includes the upper surface side portion of the inner housing, and the bottom surface side portion of the inner housing includes a bottom surface side portion of the inner housing. The upper surface side portion and the bottom surface side portion of the inner housing are joined together at a first bond line to form the first side surface of the inner housing. The second bond line of the inner housing is provided on the first side surface and extends between the front end and the back end of the ultrasonic probe. The first bond line of the probe case and the first bond line of the inner housing are vertically offset from each other.

A second aspect of the present disclosure provides an ultrasound diagnostic device with an ultrasonic probe. The ultrasonic probe provides the features of the first aspect of the present disclosure.

DETAILED DESCRIPTION

Embodiments of the present invention will be described below. Note that the invention claimed in the embodiments described herein is not limited. In particular, in the present disclosure, a medical ultrasonic diagnostic system is described as an example. However, the present invention may be applied to an ultrasonic examination system, an ultrasonic examination device, and an ultrasonic probe for the non-destructive examination of buildings, structures, various mechanical devices, and the like.

Figure 1:
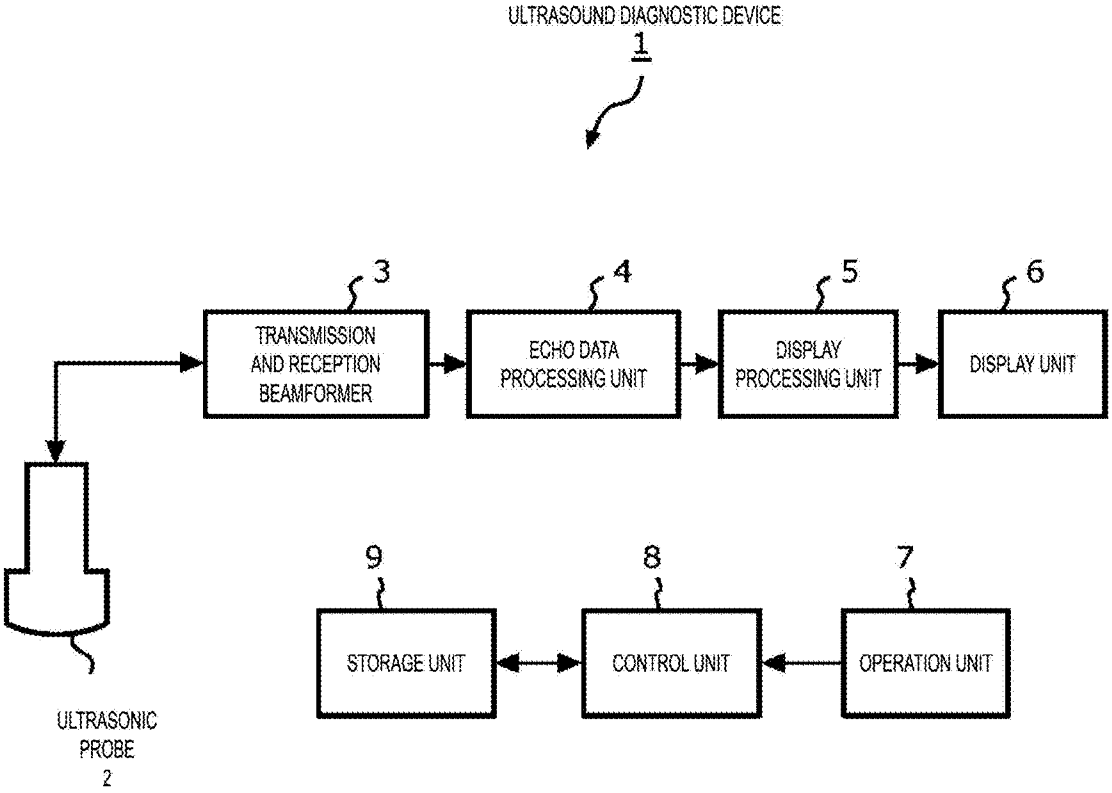
FIG. 1 is a block diagram depicting one example of a schematic configuration of an ultrasonic diagnostic system according to an embodiment.

Embodiments of the present invention will be described hereinafter with reference to the drawings. The ultrasound diagnostic device 1 depicted in FIG. 1 is provided with an ultrasonic probe 2, a transmission and reception beamformer 3, an echo data processing unit 4, a display processing unit 5, a display unit 6, an operation unit 7, a control unit 8, and a storage unit 9. The ultrasound diagnostic device 1 is has a configuration as a computer.

The ultrasonic probe 2 includes a plurality of ultrasonic transducers (see FIG. 4) disposed in an array, transmits ultrasonic waves to an examination target by the ultrasonic transducers, and receives an echo signal thereof.

The ultrasonic probe 2 transmits and receives ultrasonic waves to and from an examination target. The transmission and reception beamformer 3 supplies an electric signal for transmitting an ultrasonic wave from the ultrasonic probe 2 under a predetermined scanning condition to the ultrasonic probe 2 on the basis of a control signal from the control unit 8. Furthermore, the transmission and reception beamformer 3 performs signal processing such as A/D conversion and delay-and-sum processing on the echo signal received by the ultrasonic probe 2, and outputs the signal-processed echo data to the echo data processing unit 4.

The echo data processing unit 4 processes the echo data output from the transmission and reception beamformer 3 to create an ultrasound image. For example, echo data processing unit 4 creates B-mode data by performing B-mode processing such as logarithmic compression processing or envelope detection processing.

The display processing unit 5 scan-converts data input from the echo data processing unit 4 using a scan converter (scan converter) to create ultrasonic image data. For example, the display processing unit 5 scan-converts B-mode data to create B-mode image data and causes the display unit 6 to display an ultrasonic image on the basis of the ultrasound image data. The ultrasound image is, for example, a B-mode image on the basis of the B-mode image data.

The display unit 6 is a liquid crystal display (LCD), an organic electro-luminescence (EL) display, or the like. The operation unit 7 is a device to which a user inputs instructions and information. For example, although not particularly depicted in the drawings, the operation unit 7 includes a keyboard, and also includes a pointing device such as a mouse, a trackball, and the like.

The control unit 8 is, for example, a processor such as a central processing unit (CPU). The control unit 8 reads a program stored in the storage unit 9 and controls each unit of the ultrasound diagnostic device 1. For example, the control unit 8 reads a program stored in the storage unit 9 and causes the read program to execute the functions of the reception and transmission beamformer 3, the echo data processing unit 4, and the display processing unit 5.

The control unit 8 may execute all of the functions of the reception and transmission beamformer 3, all of the functions of the echo data processing unit 4, and all of the functions of the display processing unit 5 by a program, or may execute only a part of the functions by a program. When the control unit 8 executes only a part of the functions, the remaining functions may be executed by hardware such as a circuit. Note that the functions of the reception and transmission beamformer 3, the ultrasound data processing unit 4, and the display processing unit 5 may be implemented by hardware such as a circuit.

The storage unit 9 is a hard disk drive (HDD), a semiconductor memory (memory) such as a random-access memory (RAM) or a read-only memory (ROM), or the like.

The ultrasound diagnostic device 1 may include the HDD, the RAM, and the ROM as the storage unit 9. Furthermore, the storage unit 9 may be a portable storage medium such as a compact disk (CD) or a digital versatile disk (DVD). A program executed by the control unit 8 is stored in a non-transient storage medium such as an HDD or a ROM. Furthermore, the program may be stored in a portable non-transient storage medium such as a CD or a DVD.

Figure 2:
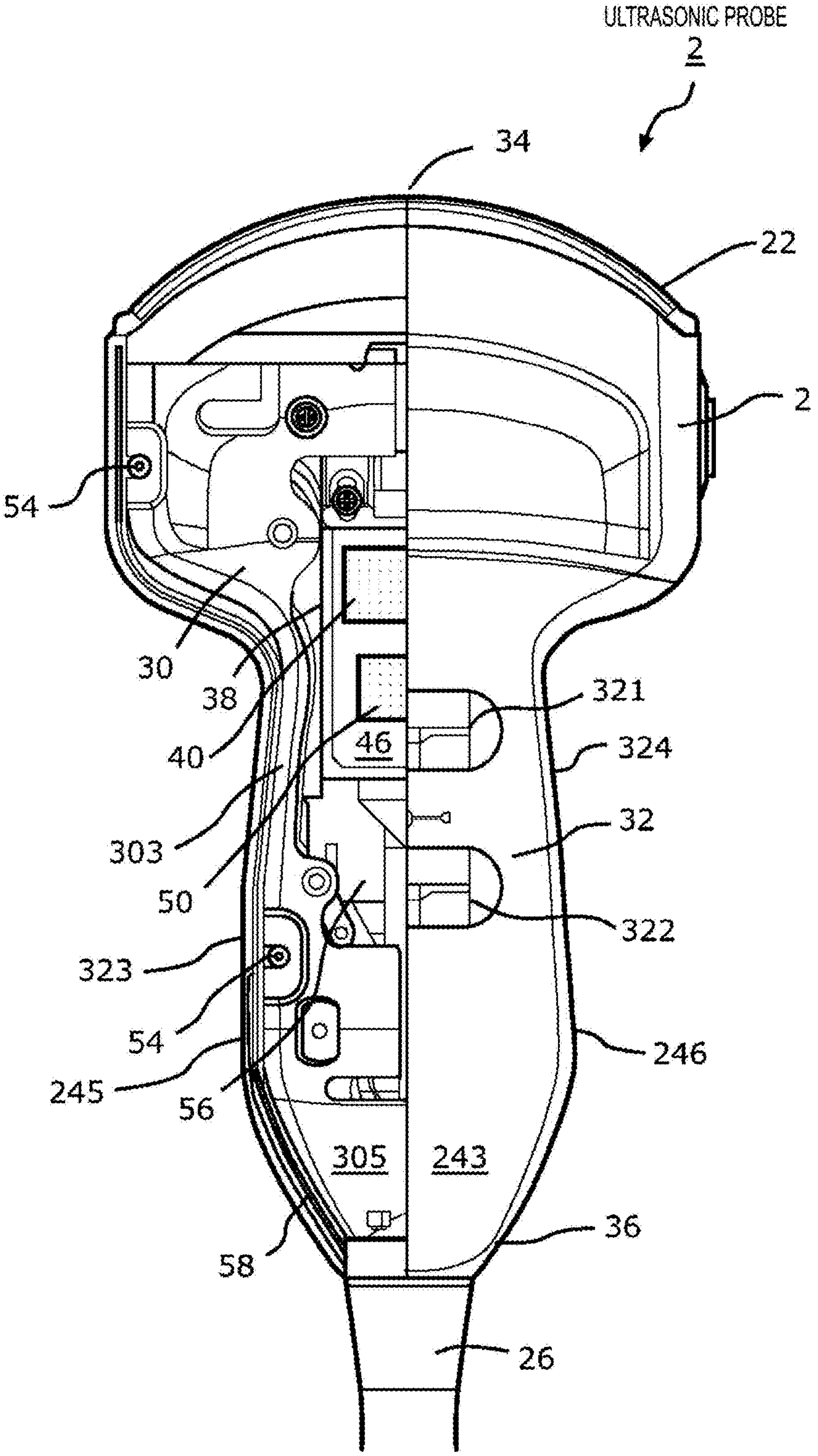
FIG. 2 is a diagram depicting an external structure and an internal structure of an ultrasonic probe according to an embodiment.
Figure 3:
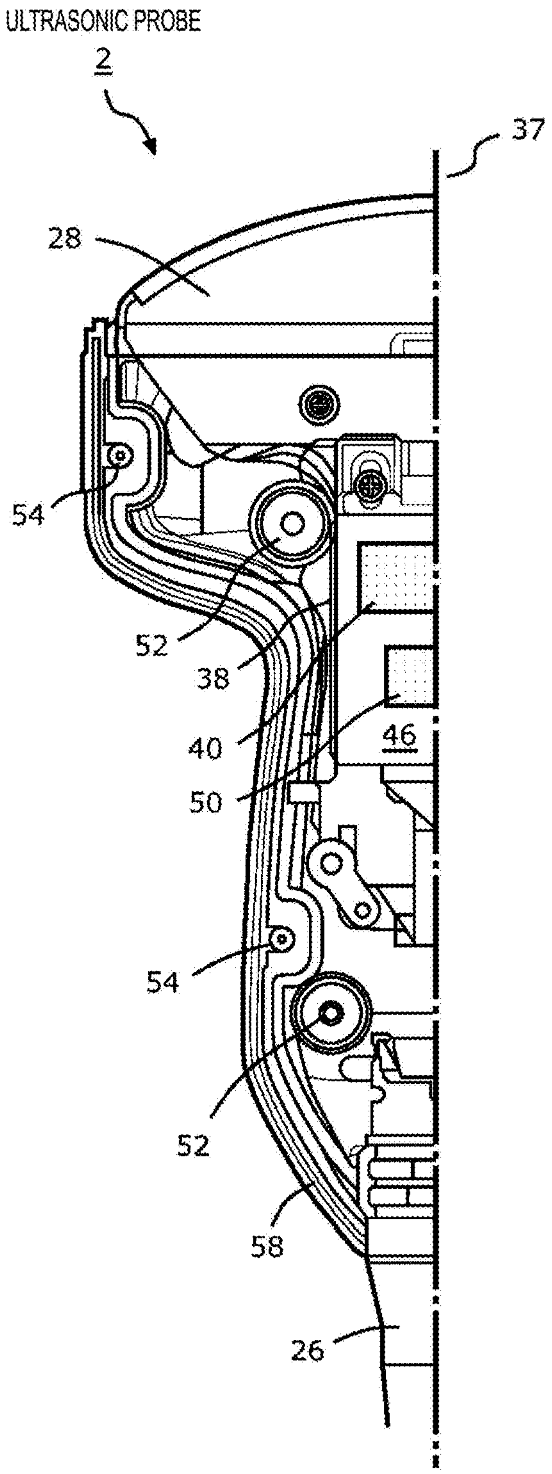
FIG. 3 is a diagram depicting the internal structure of the ultrasonic probe according to an embodiment.

FIGS. 2 and 3 are diagrams depicting an external structure and an internal structure of an ultrasonic probe 2. In the present embodiment, the ultrasonic probe 2 is a convex type ultrasonic probe, but the ultrasonic probe may also be an ultrasonic probe for a bronchial endoscope, a transesophageal ultrasonic probe, or another type of ultrasonic probe such as a linear type probe or the like. A convex type ultrasonic probe has a lens with a convex curved surface, and radiates ultrasonic waves that diverge radially. Convex type ultrasonic probes are used for abdominal ultrasound examinations, and the like. A linear type ultrasonic probe has a flat lens and emits ultrasonic waves that do not diffuse in a direction perpendicular to the contact surface. Linear ultrasonic probes are used for ultrasound echo examinations of the thyroid gland and blood vessels. Both convex and linear ultrasonic probes have a generally rectangular cross section in a plane perpendicular to a longitudinal axis extending from the front end to the back end of the ultrasonic probe.

The right side of FIG. 2 is a diagram illustrating the external structure of the ultrasonic probe 2, and the left side of FIG. 2 is a diagram illustrating the internal structure of the ultrasonic probe 2 with the upper surface side portion 241 of the probe case 24 removed. As depicted in FIG. 2, a lens 22 is provided at the front-end part 34 of the ultrasonic probe 2, and the cable 26 is provided at the back-end part 36 of the ultrasonic probe 2. An operator of the ultrasonic probe 2 holds a handle 32 and brings the lens 22 into contact with the examination target to collect ultrasound images. The ultrasonic probe 2 has a generally rectangular cross-section in a plane perpendicular to a longitudinal axis 37 extending from the front-end part 34 to the back-end part 36.

Figure 4:
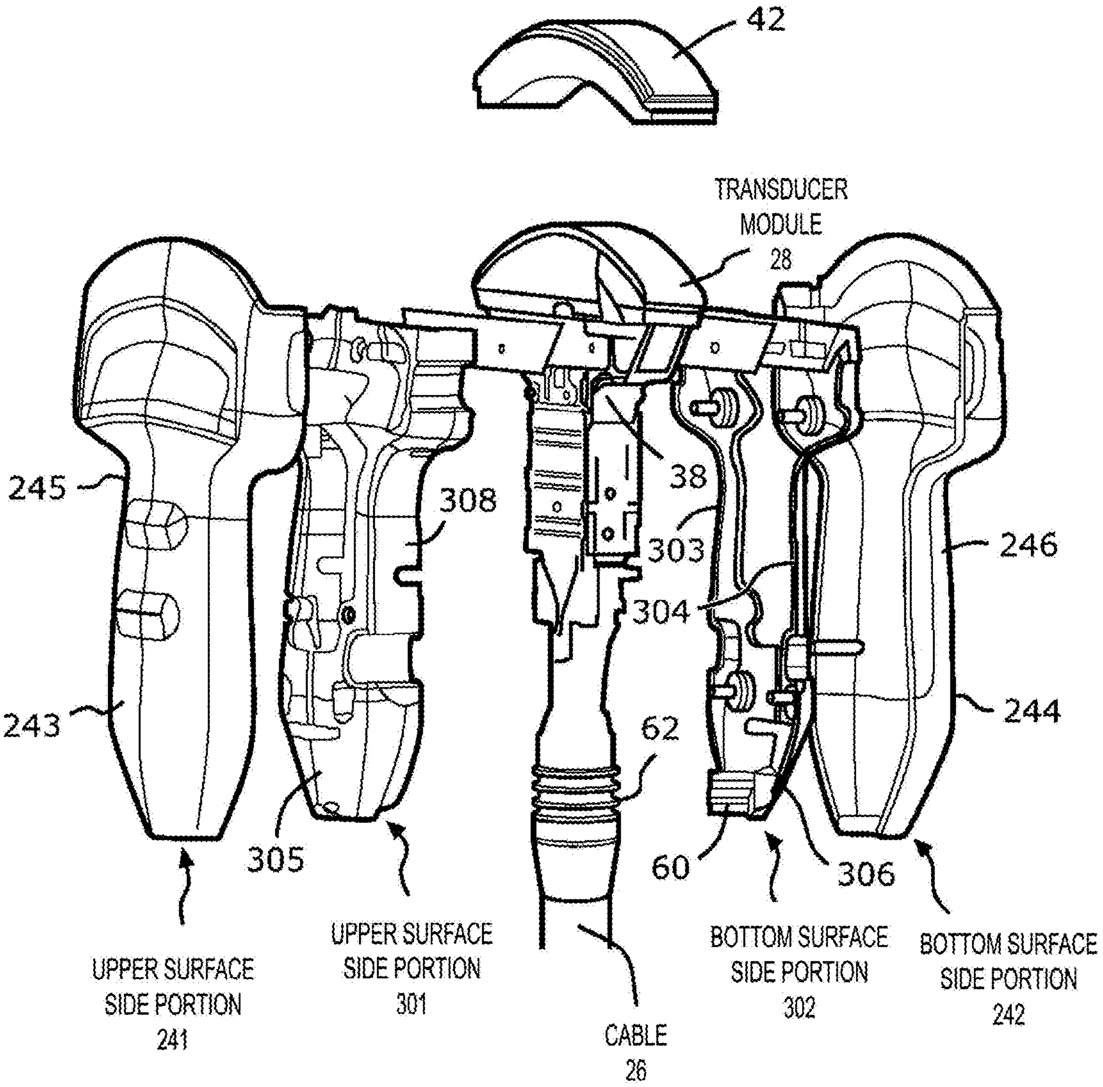
FIG. 4 is an exploded view depicting main components of the ultrasonic probe according to an embodiment.

In the embodiment of FIG. 2, as depicted in FIG. 4, the probe case 24 of the ultrasonic probe 2 is constituted by an upper surface side portion 241 provided on the front side of the paper surface of FIG. 2 and a bottom surface side portion 242 provided on the back side of the paper surface of FIG. 2. The probe case 24 may be made of resin. As depicted in FIG. 2, the bottom surface side portion 242 of the probe case 24 is provided with a plurality of protrusions 54 and the upper surface side portion 241 of the probe case 24 is provided with a plurality of holes that receive the plurality of protrusions 54 to enable precise alignment of the upper surface side portion 241 and the bottom surface side portion 242. Some or all of the plurality of protrusions 54 may be disposed on the upper surface side portion 241, and some or all of the plurality of holes that receive the protrusions 54 may be disposed on the bottom surface side portion 242. The bottom surface side portion 242 is further provided with a groove 58 at the end joined to the upper surface side portion 241 to receive a linear protrusion provided at the end of the upper surface side portion 241. The groove of the bottom surface side portion 242 and the linear protrusion of the upper surface side portion 241 may have complementary shapes that enable alignment with each other, and may be stepped portions or the like that are combined with each other.

The probe case 24 includes an upper surface 243 and a bottom surface 244 facing each other, and two side surfaces 245, 246 connected to the upper surface 243 and the bottom surface 244. Both the upper surface 243 and bottom surface 244 of the probe case 24 have a width that is greater than the height of the two side surfaces 245, 246 of the probe case 24 at most axial positions of the longitudinal axis 37. The height of the two side surfaces 245, 246 and the width of the probe case 24 are substantially the same at the back-end part 36 of the ultrasonic probe 2. In other words, the cross-section of the probe case 24 perpendicular to the longitudinal axis 37 has a shape close to a square at the back-end part 36 of the probe case 24. In a preferred embodiment of the present invention, the width is greater than the height of the two side surfaces 245, 246 of the probe case 24 at the 80 to 100% axial position. More preferably, the width is greater than the height of the two side surfaces 245, 246 of the probe case 24 at the 90 to 99% axial position. At least the upper surface side portion 241 of the probe case 24 includes the upper surface 243 of the probe case 24, and the bottom surface side portion 242 of the probe case 24 includes a bottom surface 244 of the probe case 24. Herein, a longitudinal axis 37 extending from a front-end part 34 to a back-end part 36 of the ultrasonic probe 2 extends in the length direction, a width direction extends to the left and right of the paper surface of FIG. 2, and a height direction extends perpendicular to the paper surface of FIG. 2.

A metal inner housing 30 is provided inside the probe case 24 of the ultrasonic probe 2. The outer surface of the inner housing 30 has a shape conforming to the inner surface of the probe case 24. The inner housing 30 may be manufactured by a known method such as casting, additive manufacturing, CNC processing, forging, or press working. The upper surface side portion 301 and the bottom surface side portion 302 of the inner housing 30 are bonded together by an adhesive (first adhesive). The inner surface of the probe case 24 is attached to the outer surface of the inner housing 30 by an adhesive (second adhesive). The upper surface side portion 241 and the bottom surface side portion 242 of the probe case 24 (FIG. 4) are also bonded together by an adhesive (third adhesive). The front end of the probe case 24 is adhered to the lens 22 and the back end of the probe case 24 is adhered to the cable 26. There are times when the ultrasonic probe 2 is sterilized with a sterilizing liquid and cleaned with a cleaning liquid, so the adhesive is preferably an adhesive having excellent water resistance, such as a polyvinyl chloride (PVC) resin-based adhesive or an epoxy resin-based adhesive. In terms of miniaturization, it is preferable that the thickness of the adhesive is 5 mm or less. In terms of the strength of the adhesive, it is preferable that the thickness of the adhesive is 0.3 mm or greater. More preferably, the adhesive has a thickness of 1 to 4 mm. The first to third adhesives may be the same adhesive or different adhesives.

Returning to the description of FIG. 2, both an upper surface side portion 301 and a bottom surface side portion 302 of the inner housing 30 include an opening 56. The inner housing 30 includes crossbeam members 303 and 304 extending alongside surfaces 323 and 324 of the handle 32. The opening 56 of the inner housing 30 is at least partially defined by the crossbeam members 303 and 304. The handle 32 is provided with one or more operation buttons 321 and 322, and the one or more operation buttons 321 and 322 are positioned at the position of the opening 56 of the inner housing 30. The positioning of the one or more operation buttons 321 and 322 at the position of the opening 56 of the inner housing 30 allows the one or more operation buttons 321 and 322 to sink slightly when an operator operates the one or more operation buttons 321 and 322. The operation of the operation buttons 321 and 322 may affect the air pressure inside the inner housing 30 and may apply a load to the adhesive of the inner housing 30.

Similar to the probe case 24, the inner housing 30 also includes an upper surface 305 and a bottom surface 306 facing each other, and two side surfaces 307 and 308 connected to the upper surface 305 and the bottom surface 306. Both the upper surface 305 and the bottom surface 306 of the inner housing 30 have a width that is greater than the height of the two side surfaces 307, 308 of the inner housing 30. Similar to the probe case 24, the inner housing 30 also has at least an upper surface side portion 301 and a bottom surface side portion 302. The upper surface side portion 301 of the inner housing 30 includes an upper surface 305 of the inner housing, and the bottom surface side portion 302 of the inner housing 30 includes a bottom surface 306 of the inner housing 30.

A chassis 38 is positioned in the opening 56 of the inner housing 30. A flexible printed circuit board 46 with a plurality of electronic components 40, 50 is fixed to the chassis 38. The chassis 38 is fixed to the inner housing 30 by a fastener such as a bolt so that constituent elements fixed thereto do not easily move and do not move from a predetermined position of the ultrasonic probe 2. The electronic components 40, 50 may be an integrated circuit that performs signal processing and processing related to environmental information. In certain embodiments of the present invention, the back end of the printed circuit board 46 is removably connected to the cable 26 by a connector 48 (FIG. 5), and the front end of the printed circuit board 46 is removably connected to a transducer module 28 by a connector (not depicted). Thereby power can be supplied from the cable to the electronic components 40, 50 provided on the printed circuit board 46 and the transducer module 28. Moreover, bidirectional signal transmission is possible via the printed circuit board 46 and the cable 26. The chassis 38 is detachably fixed to the inner housing 30 by a fastener such as a bolt. When a failure or the like occurs in the electronic components 40, 50, the chassis 38 including the printed circuit board 46 may be replaced with a new chassis through the opening 56 of the inner housing 30. In certain embodiments of the present invention, the chassis 38 is made of a non-magnetic material, such as a resin.

FIG. 3 is a diagram depicting the internal structure of the ultrasonic probe 2 in which the upper surface side portion 301 (FIG. 4) of the inner housing 30 and a portion of the lens 22 are removed. In the embodiment of FIG. 3, as depicted in FIG. 4, the inner housing 30 of the ultrasonic probe 2 is constituted by the upper surface side portion 301 provided on the front side of the paper surface of FIG. 3 and the bottom surface side portion 302 provided on the back side of the paper surface of FIG. 3. As depicted in FIG. 3, the bottom surface side portion 302 of the inner housing 30 is provided with a plurality of protrusions 52 and the upper surface side portion 301 of the inner housing 30 is provided with a plurality of holes that receive the plurality of protrusions 52 to enable precise alignment of the upper surface side portion 301 and the bottom surface side portion 302. Some or all of the plurality of protrusions 52 may be disposed on the upper surface side portion 301, and some or all of the plurality of holes that receive the protrusions 52 may be disposed on the bottom surface side portion 302. The bottom surface side portion 302 may be further provided with a groove at the end joined to the upper surface side portion 301 to receive a linear protrusion provided at the end of the upper surface side portion 301. The groove of the bottom surface side portion 302 and the linear protrusion of the upper surface side portion 301 may have complementary shapes that enable alignment with each other, and may be stepped portions or the like that are combined with each other. The inner housing 30 can feasibly be assembled in parts in the left-right or the up-down direction of the paper surface, rather than in the upper surface side portion 301 and the bottom surface side portion 302. In this case, however, a structure that is deep relative to the bond line must be created, which would increase costs. In contrast, if the inner housing 30 is manufactured by partitioning into an upper surface side portion 301 and a bottom surface side portion 302, a structure that is shallow relative to the bond line can be created, and manufacturing costs can be reduced. Furthermore, by partitioning the inner housing 30 into the upper surface side portion 301 and the bottom surface side portion 302, the printed circuit board 46 and the like can be attached more easily than with other partitioning methods.

The plurality of protrusions 52 of the inner housing 30 may be replaced by fasteners such as bolts and nuts. The upper surface side portion 301 and the bottom surface side portion 302 of the inner housing 30 are also bonded to each other by an adhesive. The front end of the inner housing 30 is adhered to the transducer module 28, and the back end of the inner housing 30 is adhered to the cable 26. There are times when the ultrasonic probe 2 is sterilized with a sterilizing liquid and cleaned with a cleaning liquid, so the adhesive is preferably an adhesive having excellent water resistance, such as a polyvinyl chloride (PVC) resin-based adhesive or an epoxy resin-based adhesive. While the inner housing 30 is a rigid body made of metal, the cable 26 is made of resin and has flexibility, and thus both joining portions are portions into which liquid penetrates in a relatively easy manner. In certain embodiments, the cable 26 and the inner housing 30 are provided with one or more annular grooves and one or more annular protrusions that are complementary to each other to prevent liquid from penetrating the interior of the ultrasonic probe 2. One or more rubber O-rings may be provided in the one or more annular grooves to enhance air and water tightness.

As described above, the ultrasonic transducer included in the ultrasonic probe vibrates in response to an applied voltage and generates heat because it is a constituent element that generates ultrasonic waves. In order to dissipate heat generated by the ultrasonic transducer, the ultrasonic probe may be provided with a metal inner housing 30 that is thermally connected to the ultrasonic transducer. Since the inner housing 30 must have high thermal conductivity, it must be manufactured using a metal having high thermal conductivity, such as aluminum or copper. In terms of weight reduction, aluminum is more preferable than copper. In addition, when the inner housing 30 is thin, heat accumulation around the ultrasonic transducer is prevented and heat transfer capability is lowered, so the thickness must be 1 mm or greater. On the other hand, when the inner housing 30 is too thick, the heat transfer capability improves, but the ease of processing is reduced and the weight of the ultrasonic probe cannot be reduced, so the thickness must be 5 mm or less. More preferably, the thickness of the inner housing 30 is 2 to 4 mm.

Figure 5:
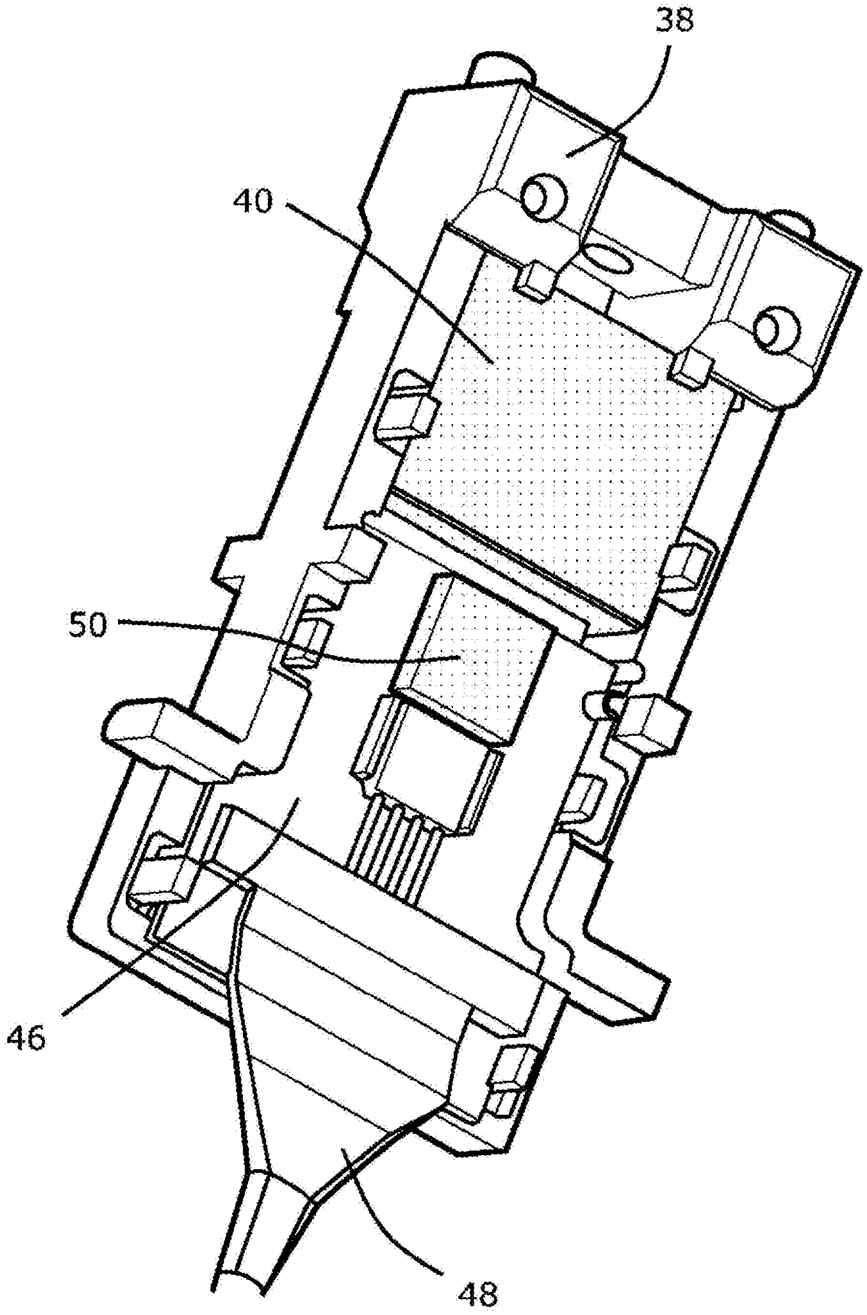
FIG. 5 is a diagram depicting a chassis built into the ultrasonic probe according to an embodiment.
Figure 6:
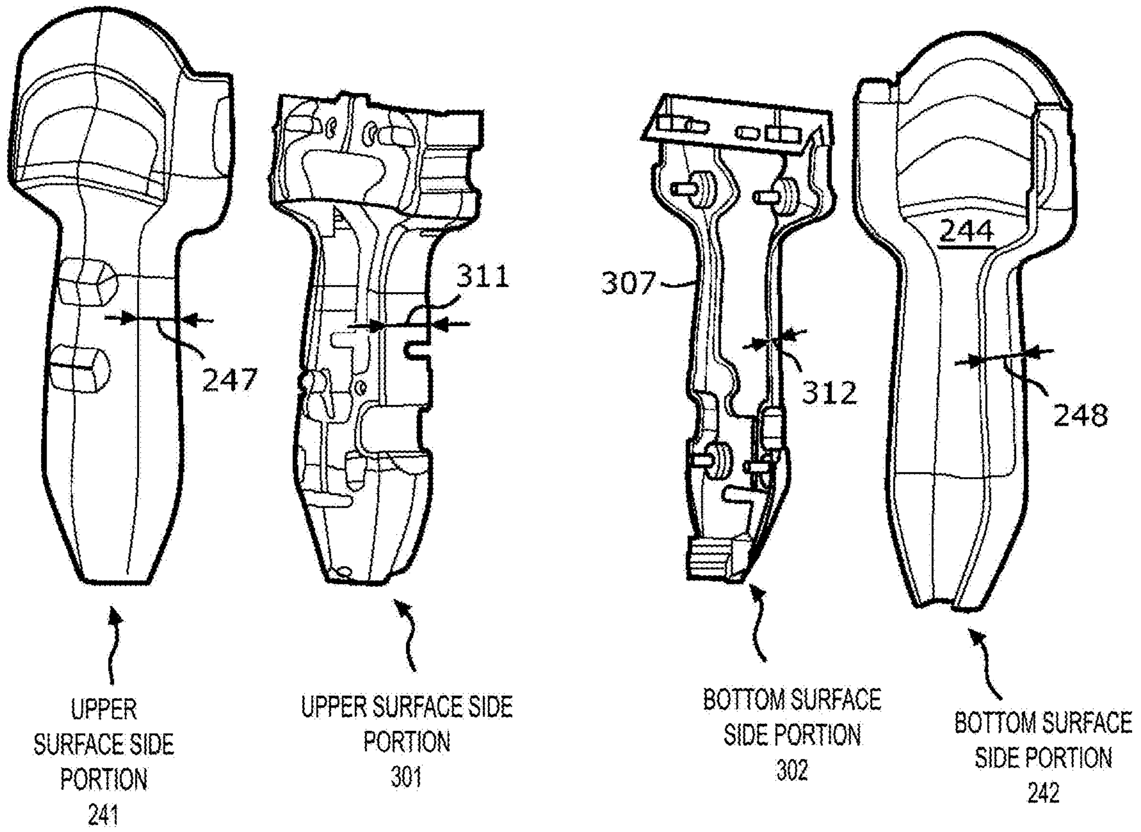
FIG. 6 is a diagram depicting a state in which an inner housing and a probe case of an ultrasonic probe are joined together according to an embodiment.

FIG. 4 is an exploded view depicting main components of the ultrasonic probe 2, and FIG. 5 is a diagram depicting the chassis 38 that is built into the ultrasonic probe 2. FIG. 6 is a diagram depicting a state in which the inner housing 30 and the probe case 24 of the ultrasonic probe 2 are joined together. In the embodiment of FIGS. 4 to 6, both the inner housing 30 and the probe case 24 have left-right symmetry. As depicted in FIG. 5, in a particular embodiment of the present invention, the printed circuit board 46 of the chassis 38 has a plurality of electronic components 40, 50. As depicted in FIG. 5, the printed circuit board 46 of the chassis 38 is connected on the back end to the connector 48 of the cable 26. The printed circuit board 46 of the chassis 38 is connected to the transducer module 28 at the front end of the chassis 38. An acoustic lens 42 is attached to the transducer module 28. Next, the upper surface side portion 301 and the bottom surface side portion 302 of the inner housing 30 are also bonded to each other so as to enclose or interpose these components. Next, the upper surface side portion 241 and the bottom surface side portion 242 of the probe case 24 are joined to each other so as to enclose or interpose these components.

The upper surface side portion 301 and the bottom surface side portion 302 of the inner housing 30 are joined together at bond lines 314, 316 on both side surfaces 307, 308 to form the side surfaces 307, 308 of the inner housing 30. As depicted in FIG. 6, in a preferred embodiment, the height 311 of the upper surface side portion 301 of the inner housing 30 is greater than the height 312 of the bottom surface side portion 302. Specifically, the height 311 of the upper surface side portion 301 is 55% to 95% of the height of the side surface 307. More preferably, the height 311 of the upper surface side portion 301 is 65% to 90% of the height of the side surface 307. The height 311 of the upper surface side portion 301 is 1.2 to 19 times the height 312 of the bottom surface side portion 302. More preferably, the height 311 of the upper surface side portion 301 is 1.8 to 9 times the height 312 of the bottom surface side portion 302. Bond lines 314, 316 of the inner housing 30 are provided on two side surfaces 307, 308, respectively. Two bond lines 314, 316 extend between the front end 34 and the back end 36 of the ultrasonic probe 2. The height 311 of the upper surface side portion 301 of the inner housing 30 may be the same or different on the two side parts. Similarly, the height 312 of the bottom surface side portion 302 of the inner housing 30 may be the same or different on the two side parts. In other embodiments, one side surface of the inner housing 30 has a bond line, but the other side surface does not have a bond line. The metal material of the inner housing 30 is thin enough to bend at the side surface where the bond line is not provided, and the adhesive bonding is only performed on the side surface where the bond line is provided.

The upper surface side portion 241 and the bottom surface side portion 242 of the probe case 24 are joined together at bond lines 250, 252 on the two side surfaces 245, 246 of the probe case 24 to form the two side surfaces 245, 246 of the probe case 24. The two bond lines 314, 316 of the probe case 24 extend between the front end 34 of the ultrasonic probe 2 and the back end 36 of the ultrasonic probe 2. As depicted in FIG. 6, in a preferred embodiment, the height 247 of the upper surface side portion 241 of the probe case 24 is approximately the same height as the height 248 of the bottom surface side portion 242 for aesthetic reasons. However, the height 247 of the upper surface side portion 241 may be between 5% and 50% of the height of the side surface 245. More preferably, the height 247 of the upper surface side portion 241 can be set to 10% to 40% of the height of the side surface 245. The bond lines 250, 252 of the probe case 24 are provided on the two side surfaces 245, 246, respectively. The two bond lines 250, 252 extend between the front end 34 and the back end 36 of the ultrasonic probe 2. The height 247 of the upper surface side portion 241 of the probe case 24 may be the same or different on the two side parts. Similarly, the height 248 of the bottom surface side portion 242 of the probe case 24 may be the same or different on the two side parts. In other embodiments, one side surface of the probe case 24 has a bond line, but the other side surface does not have a bond line. The resin material of the probe case 24 is flexible and thin enough to be bendable, and the inner housing 30 can be inserted into the bag-shaped probe case 24. In this case, the probe case 24 is bonded by an adhesive only on the side surface where the bond line is provided.

Figure 7:
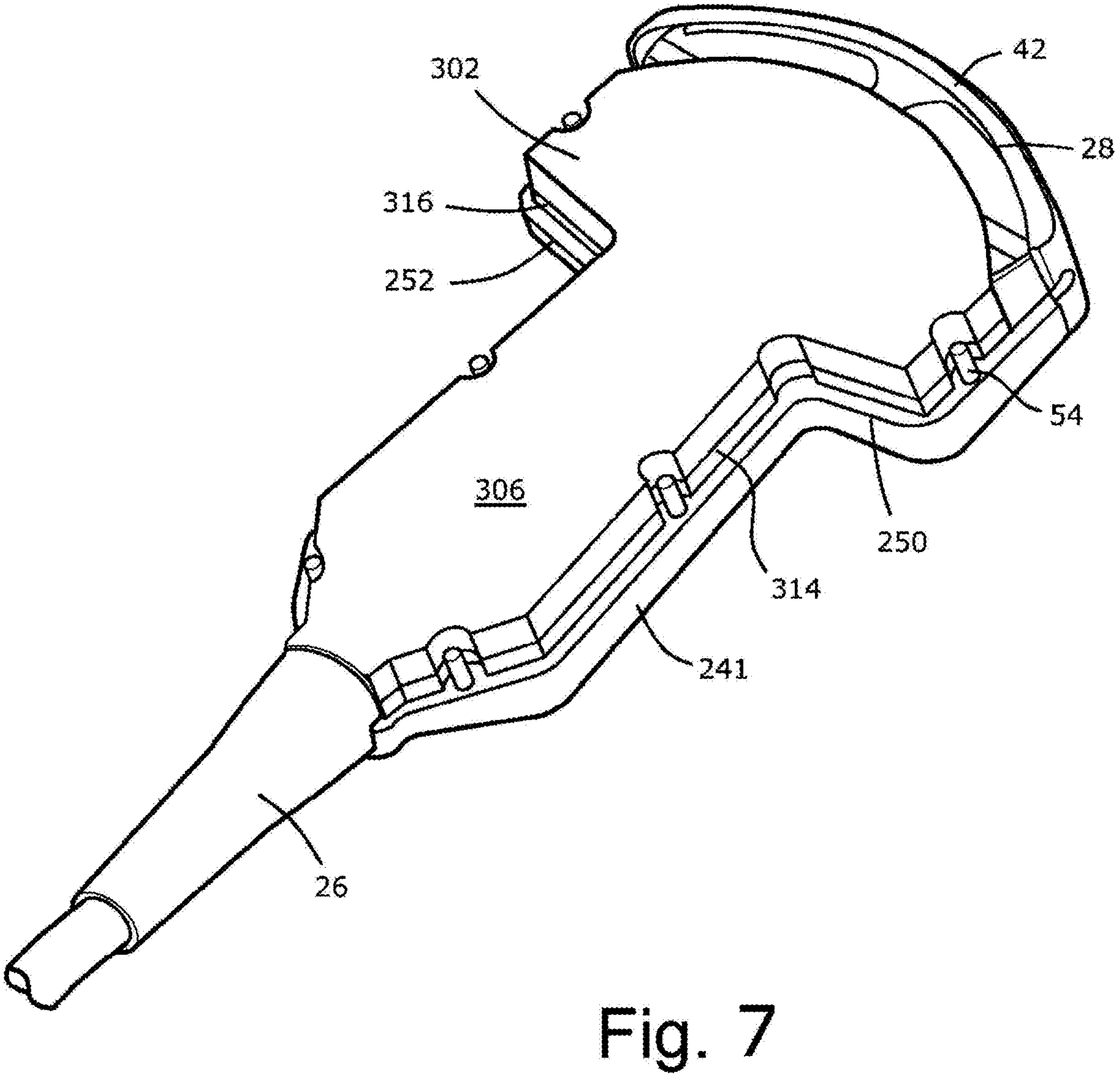
FIG. 7 is a diagram depicting a state in which an inner housing is provided in a probe case according to an embodiment.

FIG. 7 is a perspective view depicting the ultrasonic probe 2 where the bottom surface side portion 242 of the probe case 24 is removed in a specific embodiment of the present invention. As depicted in the figure, the bond line 250 on the front side of the probe case 24 and the bond line 314 on the front side of the inner housing 30 are offset in the height direction, so that the two lines are drawn as two parallel lines. The bond line 252 on the back side of the probe case 24 and the bond line 316 on the back side of the inner housing 30 are also offset in the height direction.

Figure 8:
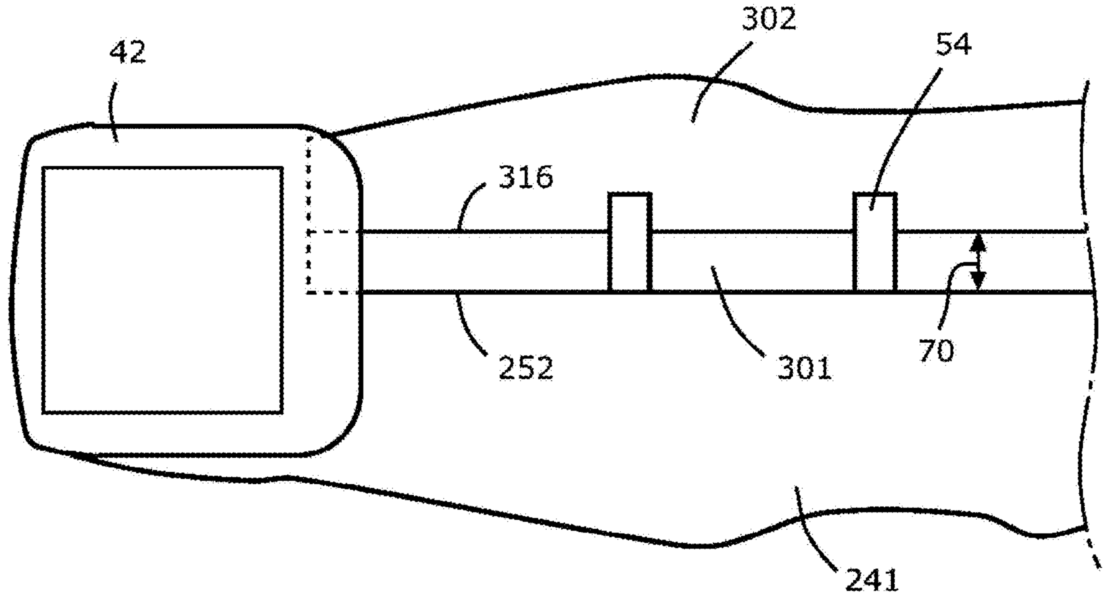
FIG. 8 is a diagram depicting the offset between the bond line on the probe case and the bond line on the inner housing according to an embodiment.

FIG. 8 is a side surface view depicting the ultrasonic probe 2 with the bottom surface side portion 242 of the probe case 24 removed in a specific embodiment of the present invention. In this side surface view, the longitudinal axis 37 of the ultrasonic probe 2 extends in the left-right direction of the drawing, and the height direction extends in the up-down direction of the drawing. As depicted in the figures, the bond line 316 of the inner housing 30 and the bond line 252 of the probe case 24 are offset vertically from the front-end part 34 to the back-end part 36 by the offset height 70. In other words, the two bond lines 252, 316 are offset from one another in the height direction. The offset height 70 is preferably between 3 mm and the height of the probe case 24, more preferably between 4 mm and 20 mm, and even more preferably between 5 mm and 15 mm. In this example, the height 247 of the upper surface side portion 241 of the probe case 24 is approximately the same as the height 248 of the bottom surface side portion 242. On the other hand, the height 311 of the upper surface side portion 301 of the inner housing 30 is higher than the height 312 of the bottom surface side portion 302 by twice the offset height 70.

With this structure, when a chemical penetrates through the bond line 252 of the probe case 24, the chemical must pass through a distance of at least the offset height 70 between the probe case 24 and the inner housing 30 before the chemical penetrates the bond line 316 of the inner housing 30, thereby providing strong chemical resistance and water resistance. In certain embodiments, an adhesive is filled between the probe case 24 and the inner housing 30. Filling the gap between the probe case 24 and the inner housing 30 with adhesive not only improves strength but also improves thermal conductivity. When describing the improvement of chemical resistance and water resistance, for example, if the offset height 70 is zero (the bond line 252 of the probe case 24 and the bond line 316 of the inner housing 30 are aligned at the same height), the liquid penetration path includes the first adhesive corresponding to the thickness of the probe case 24 at the bond line 252, the second adhesive having a thickness corresponding to the gap between the inner housing 30 and the probe case 24, and the third adhesive corresponding to the thickness of the inner housing 30 at the bond line 316. In contrast, if an offset height 70 is present, the liquid penetration path includes the third adhesive corresponding to the thickness of the probe case 24 at the bond line 252, the second adhesive with a thickness corresponding to the gap between the inner housing 30 and the probe case 24 plus the distance of the offset height 70, and the first adhesive corresponding to the thickness of the inner housing 30 at the bond line 316.

Figure 9A:
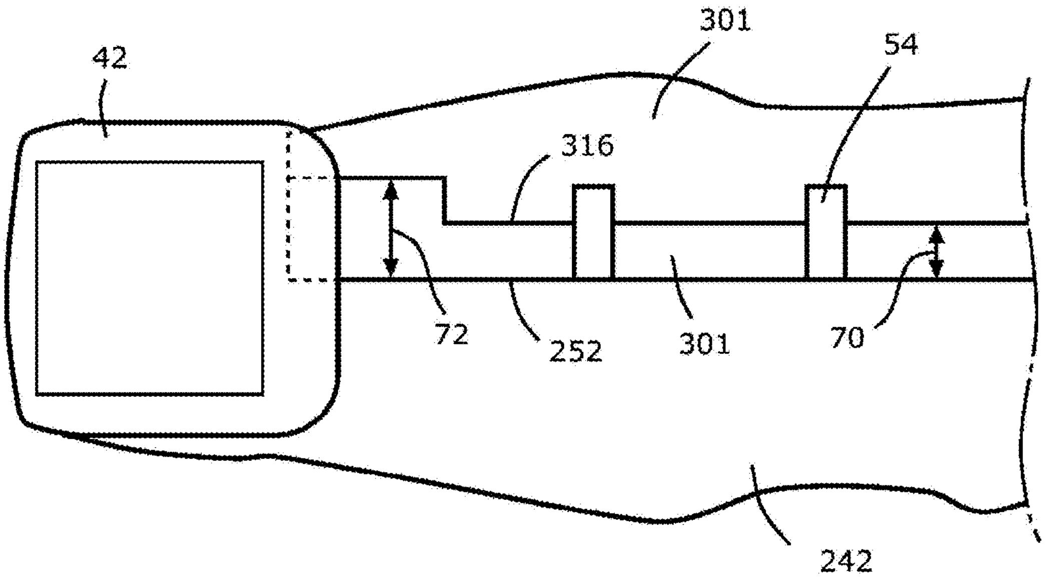
FIG. 9A is a diagram depicting the offset between the bond line on the probe case and the bond line on the inner housing according to an embodiment.
Figure 9B:
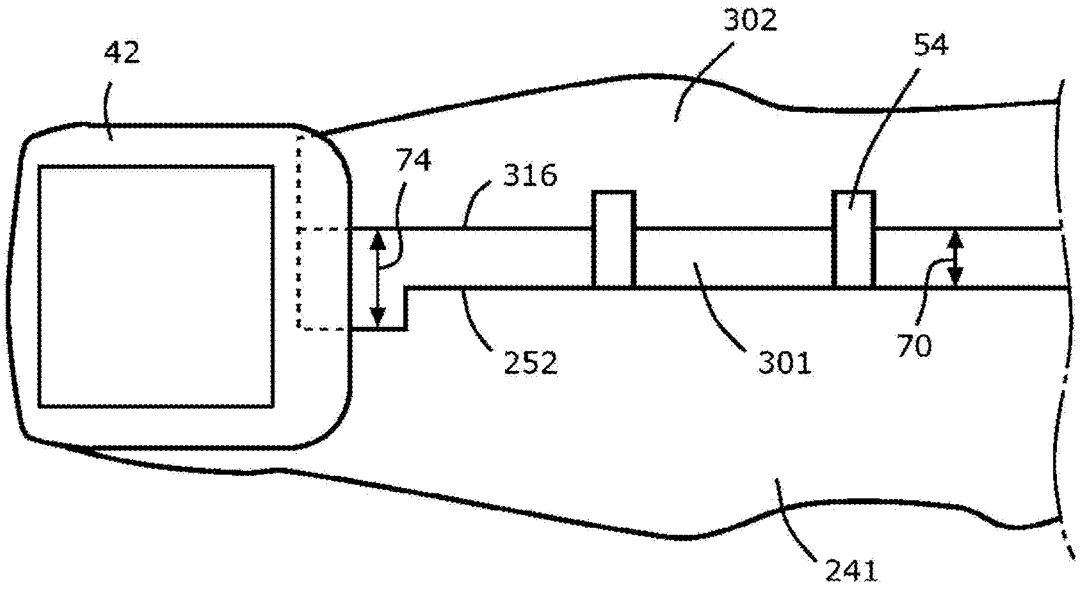
FIG. 9B is a diagram depicting the offset between the bond line on the probe case and the bond line on the inner housing according to an embodiment.

FIGS. 9A and 9B are side surface views depicting a state in which the bottom surface side portion 242 of a probe case 24 is removed from an ultrasonic probe 2 according to another embodiment of the present invention. In this side surface view as well, the longitudinal axis 37 of the ultrasonic probe 2 extends in the left-right direction of the drawing, and the height direction extends in the up-down direction of the drawing. As depicted in FIG. 9A, the bond line 252 of the probe case 24 extends straight, while the bond line 316 of the inner housing 30 is curved near the lens 22 such that the offset height 72 near the lens 22 is set higher than the offset height 70 at other locations. In the case of FIG. 9B, the bond line 252 of the probe case 24 is curved and the bond line 316 of the inner housing 30 extends linearly, so that the offset height 74 near the lens 22 is set higher than the offset height 70 at other positions. The transducer module 28 is a heat generating body, while the inner housing 30, the probe case 24, and the acoustic lens 42 are made of materials having different coefficients of thermal expansion.

Furthermore, when cleaning or disinfecting the ultrasonic probe 2, the lens 22 may be immersed in a cleaning solution or disinfectant for a long period of time. Therefore, the joint portion between the lens 22 and the probe case 24 is more likely to become a path for liquid penetration than other positions. By setting the offset height 72 near the lens 22 to be higher than the offset height 70 at other locations, the penetration path can be further lengthened, thus improving water resistance and chemical resistance. The offset heights 72, 74 are set to be 2 mm or more higher than the offset height 70, more preferably 3 mm to 10 mm higher, and even more preferably 4 mm to 10 mm higher. Although the offset heights 72, 74 both change in height by transitioning in a step-like manner, the transition may be made by a combination of various straight lines and curves.

Note that the invention is not limited to the present embodiment, and various modifications are possible without departing from the gist of the invention.

DESCRIPTION OF CODES

1. Ultrasound diagnostic device
2. Ultrasonic probe
3. Transmission and reception beamformer
4. Echo data processing unit
5. Display processing unit
6. Display unit
7. Operation unit
8. Control unit
9. Storage unit
22. Lens
24. Probe case
241. Upper surface side portion
242. Bottom surface side portion
243. Upper surface
244. Bottom surface
245, 246. Side surface
247. Upper surface height
248. Bottom surface side height
250, 252. Probe case bond line
26. Cable
28. Transducer module
30. Inner housing
301. Upper surface side portion
302. Bottom surface side portion
303, 304. Crossbeam member
305. Upper surface
306. Bottom surface
307, 308. Side surface
305. Front end part
306. Back end part
311. Upper surface side height
312. Bottom surface side height
314, 316. Inner housing bond line
32. Handle
321, 322. Operation button
323, 324. Side part
34. Front end part
36. Back end part
37. Longitudinal axis
38. Chassis
40, 50. Electronic component/integrated circuit
42. Acoustic lens
46. Printed circuit board
48. Connector
52. Protrusion
54. Protrusion
56. Opening
58. Groove
60. Circular groove
62. Annular protrusion
70, 72, 74. Offset

The invention claimed is:

1. An ultrasonic probe, comprising:
an ultrasonic transducer provided at a front end of the ultrasonic probe;
a probe case;
an inner housing provided inside the probe case;
an electronic circuit connected to the ultrasonic transducer and provided inside the inner housing; and
a lens covering the ultrasonic transducer;
wherein:
the probe case includes an upper surface and a bottom surface facing each other, and a first side surface connected to the upper surface and the bottom surface;
the upper surface and the bottom surface of the probe case both have a width greater than a height of the first side surface of the probe case;
the probe case has at least an upper surface side portion and a bottom surface side portion;
the upper surface side portion of the probe case includes the upper surface of the probe case;
the bottom surface side portion of the probe case includes the bottom surface of the probe case;
the upper surface side portion and the bottom surface side portion of the probe case are joined together at a first bond line to form the first side surface of the probe case;
the first bond line of the probe case is provided on the first side surface and extends between the front end of the ultrasonic probe and a back end of the ultrasonic probe;
the inner housing includes an upper surface and a bottom surface that face each other, and a first side surface connected to the upper surface and the bottom surface;
the upper surface and bottom surface of the inner housing both have a width greater than the height of the first side surface of the inner housing;
the inner housing has at least an upper surface side portion and a bottom surface side portion;
the upper surface side portion of the inner housing includes the upper surface of the inner housing;
the bottom surface side portion of the inner housing includes the bottom surface of the inner housing;
the upper surface side portion and the bottom surface side portion of the inner housing are joined together at a first bond line to form the first side surface of the inner housing;
the first bond line of the inner housing is provided on the first side surface and extends between the front end and the back end of the ultrasonic probe;
the first bond line of the probe case and the first bond line of the inner housing are offset from each other in a height direction; and
wherein an offset height between the first bond line of the probe case and the first bond line of the inner housing varies along the longitudinal direction, such that the offset height is greater at a first location proximate the lens than at a second location spaced from the lens.

2. The ultrasonic probe according to claim 1, wherein
the probe case includes a second side surface provided on an opposite side of the first side surface and connected to the upper surface and the bottom surface;

the upper surface and the bottom surface of the probe case both have a width greater than the height of the second side surface of the probe case;

the upper surface side portion and the bottom surface side portion of the probe case are joined together at a second bond line;

the second bond line of the probe case is provided on the second side surface and extends between the front end and the back end of the ultrasonic probe;

the inner housing includes a second side surface provided on an opposite side of the first side surface and connected to the upper surface and the bottom surface;

the upper surface and the bottom surface of the inner housing both have a width greater than the height of the second side surface of the inner housing;

the upper surface side portion and the bottom surface side portion of the inner housing are joined to one another at a second bond line;

the second bond line of the inner housing is provided on the second side surface and extends between the front end and the back end of the ultrasonic probe; and the second bond line of the probe case and the second bond line of the inner housing are mutually offset.

3. The ultrasonic probe according to claim 2, wherein the first bond line of the probe case and the second bond line of the probe case are sealed together by an adhesive.

4. The ultrasonic probe according to claim 3, further comprising:

a power supply part provided at the back end of the ultrasonic probe and connected to the electronic circuit; wherein the upper surface side portion and the bottom surface side portion of the inner housing, the ultrasonic transducer, and the power supply part are mutually sealed together to prevent liquid from penetrating into the inside of the inner housing.

5. The ultrasonic probe according to claim 2, wherein an offset height between the second bond line of the probe case and the second bond line of the inner housing varies along the longitudinal direction, such that the offset height is greater at a first location proximate the lens than at a second location spaced from the lens.

6. The ultrasonic probe according to claim 2, wherein the height of the upper surface side portion of the inner housing at the first side surface is lower than the height of the bottom surface side portion of the inner housing at the first side surface;

the height of the upper surface side portion of the inner housing at the second side surface is lower than the height of the bottom surface side portion of the inner housing at the second side surface; and the first bond line of the probe case and the first bond line of the inner housing are offset from each other in a height direction by at least 3 mm.

7. The ultrasonic probe according to claim 1, wherein the ultrasonic probe has a rectangular cross-section in a plane perpendicular to a longitudinal axis extending from the front end to the back end.

8. The ultrasonic probe according to claim 7, wherein the ultrasonic probe is a convex type or a linear type ultrasonic probe.

9. The ultrasonic probe according to claim 1, wherein the inner housing contains a metal material; and the inner housing is thermally connected to the ultrasonic transducer and configured to dissipate heat generated by the ultrasonic transducer.

10. The ultrasonic probe according to claim 4, wherein the upper surface side portion and the bottom surface side portion of the probe case, the ultrasonic transducer, and the power supply part are mutually sealed together by an adhesive to prevent liquid from penetrating into the inside of the probe case.

11. The ultrasonic probe according to claim 2, wherein the upper surface side portion and the bottom surface side portion of the inner housing both include a step having a shape complementary to a position of the first and/or second bond line of the inner housing.

12. The ultrasonic probe according to claim 1, wherein the shape of an outer surface of the inner housing is formed along a shape of an inner surface of the probe case.

13. The ultrasonic probe according to claim 4, wherein one of the upper surface side portion and the bottom surface side portion of the probe case includes a protruding part provided adjacent to the first side surface of the probe case; and the other of the upper surface side portion and the bottom surface side portion of the probe case is provided with a recessed part for receiving the protruding part.

14. The ultrasonic probe according to claim 10, wherein the power supply part includes a cable that connects to an ultrasound diagnostic device.

15. An ultrasound diagnostic device, comprising:

an ultrasonic probe comprising:

an ultrasonic transducer provided at a front end of the ultrasonic probe;

a probe case;

an inner housing provided inside the probe case;

an electronic circuit connected to the ultrasonic transducer and provided inside the inner housing; and a lens coving the ultrasonic transducer;

wherein:

the probe case includes an upper surface and a bottom surface facing each other, and a first side surface connected to the upper surface and the bottom surface;

the upper surface and the bottom surface of the probe case both have a width greater than a height of the first side surface of the probe case;

the probe case has at least an upper surface side portion and a bottom surface side portion;

the upper surface side portion of the probe case includes the upper surface of the probe case;

the bottom surface side portion of the probe case includes the bottom surface of the probe case;

the upper surface side portion and the bottom surface side portion of the probe case are joined together at a first bond line to form the first side surface of the probe case;

the first bond line of the probe case is provided on the first side surface and extends between the front end of the ultrasonic probe and a back end of the ultrasonic probe;

the inner housing includes an upper surface and a bottom surface that face each other, and a first side surface connected to the upper surface and the bottom surface;

the upper surface and bottom surface of the inner housing both have a width greater than the height of the first side surface of the inner housing;

the inner housing has at least an upper surface side portion and a bottom surface side portion;

the upper surface side portion of the inner housing includes the upper surface of the inner housing;

the bottom surface side portion of the inner housing includes the bottom surface of the inner housing;

the upper surface side portion and the bottom surface side portion of the inner housing are joined together at a first bond line to form the first side surface of the inner housing;

the first bond line of the inner housing is provided on the first side surface and extends between the front end and the back end of the ultrasonic probe;

the first bond line of the probe case and the first bond line of the inner housing are offset from each other in a height direction; and wherein an offset height between the first bond line of the probe case and the first bond line of the inner housing varies along the longitudinal direction, such that the offset height is greater at a first location proximate the lens than at a second location spaced from the lens.

16. The ultrasound diagnostic device according to claim 15, wherein the probe case includes a second side surface provided on an opposite side of the first side surface and connected to the upper surface and the bottom surface;

the upper surface and the bottom surface of the probe case both have a width greater than the height of the second side surface of the probe case;

the upper surface side portion and the bottom surface side portion of the probe case are joined together at a second bond line;

the second bond line of the probe case is provided on the second side surface and extends between the front end and the back end of the ultrasonic probe;

the inner housing includes a second side surface provided on an opposite side of the first side surface and connected to the upper surface and the bottom surface;

the upper surface and the bottom surface of the inner housing both have a width greater than the height of the second side surface of the inner housing;

the upper surface side portion and the bottom surface side portion of the inner housing are joined to one another at a second bond line;

the second bond line of the inner housing is provided on the second side surface and extends between the front end and the back end of the ultrasonic probe; and the second bond line of the probe case and the second bond line of the inner housing are mutually offset.

17. The ultrasonic probe according to claim 16, wherein the first bond line and the second bond line are sealed together by an adhesive.

18. The ultrasonic probe according to claim 17, further comprising:

a power supply part provided at the back end of the ultrasonic probe and connected to the electronic circuit; wherein the upper surface side portion and the bottom surface side portion of the inner housing, the ultrasonic transducer, and the power supply part are mutually sealed together to prevent liquid from penetrating into the inside of the inner housing.

19. The ultrasonic probe according to claim 16, wherein an offset height between the second bond line of the probe case and the second bond line of the inner housing varies along the longitudinal direction, such that the offset height is greater at a first location proximate the lens than at a second location spaced from the lens.

20. The ultrasonic probe according to claim 16, wherein the height of the upper surface side portion of the inner housing at the first side surface is lower than the height of the bottom surface side portion of the inner housing at the first side surface;

the height of the upper surface side portion of the inner housing at the second side surface is lower than the height of the bottom surface side portion of the inner housing at the second side surface; and the first bond line of the probe case and the first bond line of the inner housing are offset from each other in a height direction by at least 3 mm.

* * * * *